US005760082A

United States Patent [19]
Cook et al.

[11] Patent Number: 5,760,082
[45] Date of Patent: *Jun. 2, 1998

[54] DIETETIC FOODS CONTAINING CONJUGATED LINOLEIC ACIDS

[75] Inventors: Mark E. Cook; Michael W. Pariza, both of Madison, Wis.

[73] Assignee: Wisconsin Alumni Research Foundation, Madison, Wis.

[*] Notice: The term of this patent shall not extend beyond the expiration date of Pat. No. 5,554,646.

[21] Appl. No.: 659,845

[22] Filed: Jun. 7, 1996

Related U.S. Application Data

[63] Continuation-in-part of Ser. No. 297,472, Aug. 29, 1994, Pat. No. 5,554,646.

[51] Int. Cl.$^6$ .................. A61K 31/20; A61K 31/22; A23D 9/00
[52] U.S. Cl. .................. 514/560; 514/549; 514/558; 426/601
[58] Field of Search .................. 514/549, 558, 514/560; 426/601

[56] References Cited

U.S. PATENT DOCUMENTS

| | | | |
|---|---|---|---|
| 4,282,265 | 8/1981 | Theuer | 426/607 |
| 4,603,142 | 7/1986 | Burger et al. | 514/456 |
| 4,868,001 | 9/1989 | Maruta | 426/623 |
| 5,017,614 | 5/1991 | Pariza et al. | 514/558 |
| 5,068,119 | 11/1991 | Klemann et al. | 426/601 |
| 5,070,104 | 12/1991 | Pariza et al. | 514/549 |
| 5,162,337 | 11/1992 | Elbrecht et al. | 514/300 |
| 5,428,072 | 6/1995 | Cook et al. | 514/560 |
| 5,430,066 | 7/1995 | Cook et al. | 514/558 |
| 5,470,839 | 11/1995 | Laughlin et al. | 514/53 |
| 5,554,646 | 9/1996 | Cook et al. | 514/560 |

FOREIGN PATENT DOCUMENTS

| | | |
|---|---|---|
| 294982 | 3/1985 | Japan. |
| WO92/10105 | 6/1992 | WIPO. |

OTHER PUBLICATIONS

Y.L. Ha; N.K. Grimm and M.W. Pariza, *Carcinogenesis*, vol. 8, No. 12, pp. 1881–1887 (1987).

Y.L. Ha; N.K. Grimm and M.W. Pariza, *J. Agric. Food Chem.*, vol. 37, No. 1, pp. 75–81 (1987).

M.W. Pariza, Food Research Institute 1988 Annual Fall Meeting, Oct. 12, 1988.

The Merck Index, Tenth Edition (1983), p. 790.

The Merck Veterinary Manual, Fifth Edition (1979), pp. 1340–1343 and 1374 and 1379.

Belury, et al., "Conjugated Linoleic Acid Modulates Hepatic Lipid Composition in Mice," *Lipids* 37:199–204 (1997).

Chin, et al., "Dietary Sources of Conjugated Dienoic Isomers of Linoleic Acid, a Newly Recognized Class of Anticarcinogens," *Journal of Food Composition and Analysis* 5:185–197 (1992).

Fogerty, et al., "Octadeca-9,11-Dienoic Acid in Foodstuffs and in the Lipids of Human Blood and Breast Milk," *Nutrition Reports International* Abstract vol. 38: 937–942 (1988).

Gurr, Mike, "A trans fatty acid that is good to eat? Conjugated linoleic acid," *Lipid Technology* Nov. 133–135 (1995).

Kammerlehner, J., "Linolsaure und jonjugierte Linolsauren–ihr Vorkommen im Milchfett, ihre biologische Bedeutung," *Milchinhaltsstoffe* 26:1268–1272 (1995).

Lin, et al., "Survey of the Conjugated Linoleic Acid Contents of Dairy Products," *J Dairy Sci* 78:2358–2365 (1995).

Sarkar, G., "Beneficial ghee?," *Nature* 352:673 (1991).

Shantha, et al., "Conjugated linoleic acid concentrations in processed cheese containing hydrogen donors, iron and dairy–based additives," *Food Chemistry* 47:257–261 (1993).

Shanta, et al., "Conjugated Linoleic Acid Concentrations in Dairy Products as Affected by Processing and Storage," *Journal of Food Science* 60:695–720 (1995).

Shoichi, et al., Abstract, *Chemical Abstracts* vol. 122 (1995).

Shultz, et al., "Conjugated Linoleic Acid Concentration of Human Milk and Infant Formulae," *Human Milk and Lactation 1* p. 3187.

Sieber, R., "Konjugierte Linolsauren in Lebensmitteln: eine Ubersicht," *Nutrition* 19:265–270 (1995).

Chemical Abstracts 115:206249 (1991) Pariza.

*Primary Examiner*—Kevin E. Weddington
*Attorney, Agent, or Firm*—Quarles & Brady

[57] ABSTRACT

A dietetic food which contains a safe and effective amount of conjugated linoleic acid (CLA).

8 Claims, No Drawings

DIETETIC FOODS CONTAINING CONJUGATED LINOLEIC ACIDS

RELATED CASE

The present application is a continuation-in-part of application U.S. Ser. No. 08/297,472, filed Aug. 29, 1994, now U.S. Pat. No. 5,554,646 issued Sep. 10, 1996.

FIELD OF THE INVENTION

The present invention generally relates to human nutrition. More particularly, it relates to dietetic foods for animals, especially humans.

BACKGROUND OF THE INVENTION

Dietetic foods are synthetic foods specifically formulated for people on restricted diets. Such foods, which can contain natural foods as ingredients, can take the form of either enteral compositions or parenteral compositions.

Enteral compositions are compositions for oral consumption or tubal feeding intended to replace natural food products that cause or aggravate allergies or other conditions in some individuals. Some common examples of enteral compositions are the baby formulae which do not contain milk proteins and margarines intended for heart patients.

Parenteral compositions are compositions for intravenous administration to patients. Usually they are used with patients who have difficulty with orally administered food. Some common examples of parenteral compositions are solutions of electrolytes, proteins, carbohydrates and fats.

We have discovered that it is advantageous for humans to consume more conjugated linoleic acids (CLA) than are provided in dietetic foods. It is especially important that humans who are on restricted diets and consume only dietetic foods receive conjugated linoleic acid because such diets can be totally lacking in the CLA which can be found in some natural foods which are consumed in a normal unrestricted diet.

In addition to being a good calorie source in dietetic foods, CLA can be a valuable addition to dietetic foods because we have found it to be effective in increasing body protein or preventing the loss of body protein in a human, increasing food efficiency in humans, and reducing body fat. In addition, it appears to stimulate the immune system and to increase the level of CD4 and CD8 cells.

BRIEF SUMMARY OF THE INVENTION

It is an object of the present invention to disclose dietetic foods which contain conjugated linoleic acids (CLA).

We have discovered that dietetic foods which contain a safe amount of an active form of a conjugated linoleic acid (CLA), such as 9,11-octadecadienoic acid and 10,12-octadecadienoic acid, an ester thereof, a non-toxic salt thereof, and mixtures thereof, are a superior nutritional product for animals on restricted diets.

It will be apparent to those skilled in the art that the forementioned objects and other advantages may be achieved by the practice of the present invention.

DESCRIPTION OF THE PREFERRED EMBODIMENT

The dietetic foods of the present invention contain a safe and effective amount of an active form of conjugated linoleic acid (CLA) which is selected from a conjugated linoleic acid, such as 9,11-octadecadienoic acid and 10,12-octadecadienoic acid, an ester thereof, a non-toxic salt thereof, and mixtures thereof. These dietetic foods will also contain one or more electrolytes, proteins, carbohydrates, fats, vitamins or minerals.

The amount of the CLA to be included in the dietetic food will vary with the intended use of the food and whether the dietetic food with CLA will be the sole source of nutrition. However, since the CLA is a natural food ingredient and relatively non-toxic, the amount which can be consumed is not critical as long as it is enough to be effective and it is not contraindicated in the patient's diet.

The practice of the present invention is further illustrated by the examples which follow:

EXAMPLE 1

SYNTHESIS OF CONJUGATED LINOLEIC ACIDS (CLA) FROM LINOLEIC ACID AND SAFFLOWER OIL

Ethylene glycol (1000 g) and 500 g potassium hydroxide (KOH) are put into a 4-neck round bottom flask (5000 ml). The flask is equipped with a mechanical stirrer, a thermometer, a reflux condenser, and a nitrogen inlet. (The nitrogen introduced in first run through two oxygen traps).

Nitrogen is bubbled into the ethylene glycol and KOH mixture for 20 min and the temperature is then raised to 180° C.

1000 g of linoleic acid, corn oil, or safflower oil is then introduced into the flask. The mixture is heated at 180° C. under an inert atmosphere for 2.5 hours.

The reaction mixture is cooled to ambient conditions and 600 ml HCl is added to the mixture which is stirred for 15 min. The pH of the mixture is adjusted to pH 3. Next, 200 ml of water is added into the mixture and stirred for 5 min. The mixture is transferred into a 5 L separatory funnel and extracted three times with 500-ml portions of hexane.

The aqueous layer is drained and the combined hexane solution extracted with four 250-ml portions of 5% NaCl solution.

The hexane is washed 3 times with water. The hexane is transferred to a flask and the moisture in the hexane removed with anhydrous sodium sulfate ($Na_2 SO_4$). The hexane is filtered through Whatman paper into a clean 1000 ml round bottom flask and the hexane removed under vacuum with a rotoevaporator to obtain the CLA. The CLA is stored in a dark bottle under argon at −80° C. until time of use.

This method can be modified so as to utilize only food-grade reagents and solvents as listed in *Food Chemicals Codex*, third edition, National Academy Press, 1981.

The active forms of CLA include, in addition to the free acids, the non-toxic salts thereof, the active esters thereof, such as triglycerides, and mixtures thereof.

The free conjugated linoleic acids (CLA) have been previously isolated from fried meats and described as anti-carcinogens by Y. L. Ha, N. K. Grimm and M. W. Pariza, in Carcinogenesis Vol. 8, No. 12, pp. 1881–1887 (1987). Since then, they have been found in some processed cheese products. Y. L. Ha, N. K. Grimm and M. W. Pariza, in J. Agric. Food Chem., Vol. 37, No. 1, pp. 75–81 (1987). The free acid forms of the CLA may be prepared by isomerizing linoleic acid. The terms "conjugated linoleic acids" and "CLA" as used herein are intended to include 9,11-octadecadienoic acid, 10,12-octadecadienoic acid; non-toxic salts thereof; esters thereof; and mixtures thereof. The non-toxic salts of the free acids may be made by reacting the free acids with a non-toxic base.

One method of synthesizing CLA is described in Example 1. However, CLA may also be prepared from linoleic acid by the action of a linoleic acid isomerase from a harmless microorganism, such as the Rumen bacterium *Butyrivibrio fibrisolvens*. Harmless microorganisms in the intestinal tracts of rats and other monogastric animals may also convert linoleic acid to CLA (S. F. Chin, J. M. Storkson, W. Liu, K. Allbright and M. W. Pariza, 1994, J. Nutr. 124: 694–701.

The CLA obtained by the practice of the described methods of preparation contains one or more of the 9,11-octadecadienoic acids and/or 10,12-octadecadienoic acids and active isomers thereof. It may be free or bound chemically through ester linkages. The CLA is heat stable and can be used as is, or dried and powdered. The CLA is readily converted into a non-toxic salt, such as the sodium or potassium salt, by reacting chemically equivalent amounts of the free acid with an alkali hydroxide at a pH of about 8 to 9. CLA also can be esterified to glycerol to form mono-, di-, and triglycerides.

Theoretically, 8 possible geometric isomers of 9,11- and 10,12-octadecadienoic acid (c9, c11; c9,t11; t9,c11; t9,2t11; c10,c12; c10,t12; t10,c12 and t10,t12) would form from the isomerization of c9,c12-octadecadienoic acid. As a result of the isomerization, only four isomers (c9,c11; c9,t11; t10, c12; and c10,c12) would be expected. However, of the four isomers, c9,t11- and t10,c12- isomers are predominantly produced during the autoxidation or alkali-isomerization of c9,c12-linoleic acid due to the co-planar characteristics of 5 carbon atoms around a conjugated double-bond and spatial conflict of the resonance radical. The remaining two c,c-isomers are minor contributors.

The relatively higher distribution of the t,t-isomers of 9,11- or 10,12-octadecadienoic acid apparently results from the further stabilization of c9,t11- or t10,c12-geometric isomers, which is thermodynamically preferred, during an extended processing time or long aging period. Additionally the t,t-isomer of 9,11- or 10,12-octadecadienoic acid that was predominantly formed during the isomerization of linoleic acid geometrical isomers (t9,t12-, c9,t12- and t9,c12-octadecadienoic acid) may influence the final ratio of the isomers or the final CLA content in the samples.

Linoleic acid geometrical isomers also influence the distribution of minor contributors (c,c-isomers of 9,11- and 10,12-, t9,c11- and c11,t12-octadecadienoic acids). The 11,13-isomer might be produced as a minor product from c9,c12-octadecadienoic acid or from its isomeric forms during processing.

The exact amount of CLA to be incorporated into a dietetic food, of course, depends upon the intended use of the food, the form of CLA employed, and the route of administration. It also can depend upon the isomer ratios. However, generally the dietetic food will contain the equivalent of about 0.05 to about 1.0% of CLA by weight of the dietetic food. The CLA content also can be expressed as the amount of CLA based on the total calories in the serving e.g. 0.03 to 3 gram CLA per 100 calorie serving. Alternatively, the amount of CLA can be expressed as a percentage of the lipid or fat in the food, such as 0.3% to 100% of the food lipid, or as an amount of CLA per gram of food lipid, such as 3 to 1000 mg CLA per gram of lipid.

When the patient's sole source of food is the dietetic food, the amount of CLA employed should be such that the patient consuming the dietetic food will obtain from about 500 parts per million (ppm) to about 10,000 ppm of CLA in his diet. If the dietetic food is not the sole source of food higher or lower amounts of the dietetic food might need to be consumed to reach these levels. However, the upper limit of the amount to be employed is not critical because CLA is relatively non-toxic and it is a normal constituent of the human diet (including human breast milk).

The CLA to be incorporated into the dietetic food can be in the form of the free acid, a salt thereof; an ester thereof, such as a triglyceride; and any mixtures thereof.

EXAMPLE 2

A liquid dietetic food for parenteral administration to humans contains emulsified fat particles of about 0.33–0.5 µm in diameter. In addition, the emulsions can contain Water for Injection USP as a diluent, egg phosphatides (1–2%) as an emulsifying agent and glycerin (2–3%) to adjust toxicity. These emulsions can be infused intravenously to patients requiring parenteral nutrition. Representative formulae of the present invention would contain the same ingredients plus 0.5 mg/gm to 10 mg/gm of CLA or alternatively, 0.3% to 100% CLA based on the food lipid or 0.03 gram to 0.3 gram per 100 calorie serving. For such parenteral foods the CLA usually should be present in the form of the triglycerides.

EXAMPLE 3

A milk protein-free, soy protein-based, baby formula is prepared which contains CLA. Such a baby formula will contain about 0.5 mg/gram to about 10 mg/gram of CLA or about 0.03 gram to 0.5 gram CLA per 100 calorie serving or 0.3% to 100% CLA based on the lipid in formula.

One serving (100 calories) of a representative formula can contain the following:

| | |
|---|---|
| Protein | 2.66 g |
| Fat | 5.46 g |
| Carbohydrate | 10.1 g |
| Water | 133 g |
| CLA | 0.3 g |
| Vitamins and Minerals | (RDA amounts) |

EXAMPLE 4

A dietetic margarine of the present invention for use in a heart-healthy diet is a semi-solid or solid vegetable oil-based margarine which, in addition to the usual ingredients, contains CLA. Such a margarine will contain about 0.25 mg/gram to about 10 mg/gm of CLA or about 0.03 gram to 0.5 gm CLA per 100 calorie serving.

EXAMPLE 5

A low residue liquid enteral dietetic product useful as a high-protein, vitamin and mineral supplement contains added CLA. The amount of CLA present can be about 0.05% to about 5% by weight of CLA or about 0.3% to about 100% of the lipid present or about 0.03 to 0.3 gram CLA per 100 calories.

One serving (140 calories) of a representative formula can contain the following:

| | |
|---|---|
| Protein (egg white solids) | 7.5 g |
| Fat (CLA) | 0.1 g |
| Carbohydrate (sucrose, hydrolyzed corn starch) | 27.3 g |

| | |
|---|---|
| Water | 1.9 g |
| Vitamins and Minerals | (RDA amounts) |

It will be readily apparent to those skilled in the art that many dietetic foods, including those described in U.S. Pat. Nos. 4,282,265 and 5,470,839, can be improved by adding CLA to the food or by replacing some of the fat in the food with CLA.

It also will be readily apparent to those skilled in the art that a number of modifications or changes may be made without departing from the spirit and scope of the present invention. Therefore, the invention is only to be limited by the claims.

We claim:

1. A dietetic food for a human or non-human animal, the dietetic food comprising:
   an ingredient incorporated into the food, the ingredient selected from the group consisting of a prepared conjugated linoleic acid, an ester thereof, a non-toxic salt thereof, and mixtures thereof; said ingredient being present in an amount of at least 3 mg per gram of lipid in the food.

2. A dietetic food of claim 1 in which the dietetic food is a baby formula.

3. A dietetic food of claim 1 in which the dietetic food is suitable for enteral administration.

4. A dietetic food of claim 1 in which the ingredient is present as an ester and the dietetic food is suitable for parenteral administration.

5. In a dietetic food for a human or non-human animal, the improvement which comprises incorporating in said food a safe amount of an ingredient selected from the class consisting of a prepared conjugated linoleic acid, a salt thereof, an ester thereof, and mixtures thereof.

6. A food of claim 5 in which the amount of the ingredient is equivalent to at least about 3.0 mg of CLA per gram of product lipid.

7. A dietetic food as claimed in claim 1 wherein the ingredient is selected from chemically synthesized CLA, CLA produced by an organism, and CLA produced by an enzymatic activity.

8. A dietetic food adapted for infant feeding as the sole item of diet, said food comprising assimilable carbohydrate, protein and fat, wherein the fat comprises prepared CLA incorporated into the food so that CLA is present in the food at a level of at least about 3.0 mg per gram of fat.

* * * * *

(12) REEXAMINATION CERTIFICATE (4285th)
United States Patent
Cook et al.

(10) Number: US 5,760,082 C1
(45) Certificate Issued: Mar. 6, 2001

(54) DIETETIC FOODS CONTAINING CONJUGATED LINOLEIC ACIDS

(75) Inventors: Mark E. Cook; Michael W. Pariza, both of Madison, WI (US)

(73) Assignee: Wisconsin Alumni Research Foundation, Madison, WI (US)

Reexamination Request:
No. 90/005,034, Jul. 6, 1998

Reexamination Certificate for:
Patent No.: 5,760,082
Issued: Jun. 2, 1998
Appl. No.: 08/659,845
Filed: Jun. 7, 1996

(*) Notice: This patent is subject to a terminal disclaimer.

Related U.S. Application Data

(63) Continuation-in-part of application No. 08/297,472, filed on Aug. 29, 1994, now Pat. No. 5,554,646.

(51) Int. Cl.[7] .................. A61K 31/20; A61K 31/22; A23D 9/00
(52) U.S. Cl. .................. 514/560; 514/549; 514/558; 426/601
(58) Field of Search .................. 514/560, 549, 514/558; 426/601

(56) References Cited

U.S. PATENT DOCUMENTS 5,045,338   9/1991   Klemann et al. .................. 426/611
5,554,646 *   9/1996   Cook et al. .................. 514/560

FOREIGN PATENT DOCUMENTS

PCT/US90/00630   2/1990   (WO).

OTHER PUBLICATIONS

Chin, et al., "Conjugated Linoleic Acid is a Growth Factor for Rats as Shown by Enhanced Weight Gain and Improved Feed Efficiency," *J. Nutri.* 124:2344–2349 (1994).

Ha, et al., "Inhibition of Benzo(a)pyrene–induced Mouse Forestomach Neoplasia by Conjugated Dienoic Derivatives of Linoleic Acid," *Cancer Research* 50:1097–1101 (1990).

Ip, et al., "Mammary Cancer Prevention by Conjugated Dienoic Derivative of Linoleic Acid," *Cancer Research* 51:6118–6124 (1991).

Miller, et al., "Feeding Conjugated Linoleic Acid to Animals Partially Overcomes Catabolic Responses Due to Endotoxin Injection," *Biochemical and Biophysical Research Communications* 198:1107–1112 (1994).

Pariza, Michael W., "CLA, A New Cancer Inhibitor in Dairy Products," *Bulletin of the IDF* 257:29–30 (1991).

Pariza, Michael W., "Designer Foods: Effects on Development of Cancer," *Journal of the National Cancer Institute Monographs* 12:105–107 (1992).

Pariza, M. W., "Report of the Council on Scientific Affairs," *Archives of Internal Medicine* 153:50–56 (1993).

Pariza, M. W., "CLA and HEMF: Newly Recognized Anticarcinogenic Antioxidants," *Active Oxygens, Lipid Peroxides, and Antioxidants* (Yagi, K. ed., 359–365, Japan Sci. Soc. Press. Tokyo/CRC Press. Boca Raton (1993)).

* cited by examiner

Primary Examiner—Kevin E. Weddington

(57) ABSTRACT

A dietetic food which contains a safe and effective amount of conjugated linoleic acid (CLA).

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–8 is confirmed.

New claims 9–16 are added and determined to be patentable.

*9. A dietetic food for a human or non-human animal, the dietetic food comprising:*
  *a reduced fat food; and*
  *an ingredient incorporated into the food, the ingredient selected from the group consisting of a prepared conjugated linoleic acid, an ester thereof, a non-toxic salt thereof, and mixtures thereof; said ingredient being present in an amount of at least 3 mg per gram of lipid in the food.*

*10. A dietetic food of claim 9 in which the dietetic food is a baby formula.*

*11. A dietetic food of claim 9 in which the dietetic food is suitable for enteral administration.*

*12. A dietetic food of claim 9 in which the ingredient is present as an ester and the dietetic food is suitable for parenteral administration.*

*13. In a reduced fat dietetic food for a human or non-human animal, the improvement which comprises incorporating in said food a safe amount of an ingredient selected from the class consisting of a prepared conjugated linoleic acid, a salt thereof, an ester thereof, and mixtures thereof.*

*14. A food of claim 13 in which the amount of the ingredient is equivalent to at least about 3.0 mg of CLA per gram of product lipid.*

*15. A dietetic food as claimed in claim 9 wherein the ingredient is selected from chemically synthesized CLA, CLA produced by an organism, and CLA produced by an enzymatic activity.*

*16. A reduced fat dietetic food adapted for infant feeding as the sole item of diet, said food comprising assimilable carbohydrate, protein and fat, wherein the fat comprises prepared CLA incorporated into the food so that CLA is present in the food at a level of at least about 3.0 mg per gram of fat.*

\* \* \* \* \*